United States Patent [19]

Woltersdorf, Jr. et al.

[11] 4,196,292

[45] Apr. 1, 1980

[54] 6-SUBSTITUTED AMILORIDE DERIVATIVES

[75] Inventors: Otto W. Woltersdorf, Jr., Chalfont; Susan J. deSolms, Norristown; Edward J. Cragoe, Jr., Lansdale, all of Pa.

[73] Assignee: Merck & Co., Inc., Rahway, N.J.

[21] Appl. No.: 811,011

[22] Filed: Jun. 29, 1977

[51] Int. Cl.$^2$ .............. C07D 241/34; A61K 31/495
[52] U.S. Cl. ................................. 544/407; 424/250
[58] Field of Search .............. 260/250 BN, 250 B; 544/407

[56] References Cited

U.S. PATENT DOCUMENTS

| 3,507,865 | 4/1970 | Jones et al. | 260/250 |
| 3,573,306 | 3/1971 | Shepard et al. | 260/250 |

FOREIGN PATENT DOCUMENTS 286896  7/1968  United Kingdom ............ 260/250

*Primary Examiner*—Alton D. Rollins
*Assistant Examiner*—Lisa Jones
*Attorney, Agent, or Firm*—Michael C. Sudol, Jr.

[57] ABSTRACT

N-amidino-3,5-diamino-6-substituted-2-pyrazinecarboxamides and a process for their synthesis.

1 Claim, No Drawings

6-SUBSTITUTED AMILORIDE DERIVATIVES

SUMMARY AND BACKGROUND OF THE INVENTION

This invention relates to a novel process for preparing N-amidino-3,5-diamino-6-substituted-2-pyrazinecarboxamide particularly the N-amidino-3,5-diamino-6-chloro-2-pyrazinecarboxamide which is commercially known as amiloride. Also included are several novel N-amidino-3,5-diamino-6-substituted-2-pyrazinecarboxamides. These compounds are useful because they possess diuretic and naturetic properties. They differ from most of the known, effective diuretic agents, however, in that the compounds of this invention selectively enhance the excretion of sodium ions without causing an increase in excretion of potassium ions. The potassium loss, which is caused by known diuretics, often results in a severe muscular weakness. Since the compounds of this invention are essentially free of this potassium depletion, they have this decided advantage as diuretics. As diuretic agents, they can be used for the treatment of edema, hypertension and other diseases knwon to be responsive to this therapy.

In some instances it may be desirable to make a salt of these compounds, using a pharmaceutically acceptable acid, and these salts are to be considered as included in this invention and in the scope of the claims.

The products of this invention can be administered to man or animals in the form of pills, tablets, capsules, elixirs, injectable preparations and the like and can comprise one or more of the compounds of this invention as the only essential active ingredient of the pharmaceutical formulation or, as mentioned above, the novel compound(s) can be combined in pharmaceutical formulations with other diuretic agents or, indeed, other therapeutic agents.

The compounds of this invention are advantageously administered at a dosage range of from about 5 mg./day to about 750 mg./day or at a somewhat higher or lower dosage at the physician's discretion, preferably in subdivided amounts on a 2 to 4 times a day regimen.

Particular compounds which can be prepared according to the process of this invention are shown below in Formula I.

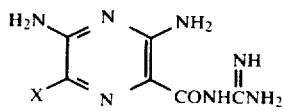

wherein X is Cl (this would be amiloride), CN, CH₃S, CF₃S. or C₆H₅S.

The novel process used to prepare these compounds is depicted in the following flow sheet:

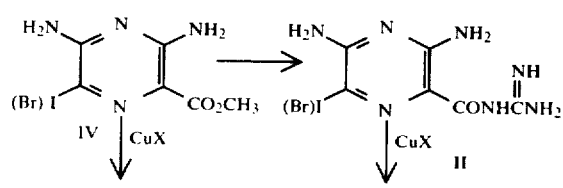

-continued

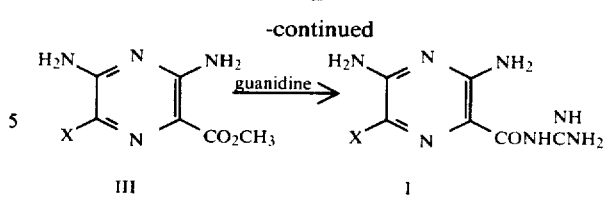

Generally the process shown as going from compound IV to II to I concerns the reaction of N-amidino-5-diamino-6-iodo (or 6-bromo)-2-pyrazinecarboxamide shown in Formula II and being described in the prior art particularly U.S. Pat. No. 3,318,813 with Cu X salts wherein X is as previously defined.

This reaction can be run in a solvent, particularly an inert organic solvent and preferably hexamethylphosphonamide or dimethylformamide. The reaction temperature is not critical and the reaction can be run at anywhere from 25°–100° C. The length of time the reaction is carried out is not critical either and can be run anywhere from 0.1 to 10 hours. Isolation of the reaction product which is N-amidino-3,5-diamino-6-X-2-pyrazinecarboxamide from the reaction mixture is performed by methods known in the art such as by adding crushed ice and water to the reaction mixture to precipitate the desired product.

An alternative route to the compounds of this invention involves the reaction of CuX wherein X is as defined above with lower alkyl (methyl)-3,5-diamino-6-iodo-(or bromo)-pyrazinoate which in turn under similar reaction conditions as discussed for the first reaction above will provide lower alkyl-3,5-diamino-6-substituted pyrazinoate. This is shown in the above flow sheet as a reaction of IV to III. Compound IV is known from the literature particularly U.S. Pat. No. 3,313,813. The lower alkyl 3,5-diamino-6-X-pyrazinoate (Compound III) can then be reacted with quanidine to yield the desired product Compound I. This latter reaction is preferably carried out under anhydrous conditions with or without a solvent such as methanol, ethanol, isopropyl alcohol or other solvents. The reaction may be carried out at room temperature or by heating on a steam bath for 1 minute to 2 hours or longer. The desired product usually is recovered from the cooled reaction mixture by trituration with water. Purification frequently is carried out by converting the product to a salt which can be recrystallized or the base can be regenerated by addition of aqueous alkali.

The following examples illustrate but do not limit the preparation of the various compositions of the invention.

EXAMPLE 1

Preparation of N-Amidino-3,5-diamino-6-cyano-2-pyrazinecarboxamide

N-Amidino-3,5-diamino-6-iodo-2-pyrazinecarboxamide hydrochloride (3.50 g., 0.01 mole), cuprous cyanide (2.15 g., 0.024 mole) and hexamethylphosphoramide (30 ml.) are combined and heated at 100° C. for 15 minutes. After cooling to ambient temperature the reaction mixture is added to aqueous sodium cyanide solution (100 ml.), stirred at 25° C. for ½ hour and the solid precipitate is collected by suction filtration, washed with water, then chloroform. On dissolving the product in boiling water (50 ml.), treating with 6 N HCl and cooling one obtains 1.43 g. of N-amidino-3,5-diamino-6-cyano-2-pyrazinecarboxamide, m.p. >350° C.

Elemental analysis for $C_7H_8N_8O.HCl.\frac{1}{2}H_2O$: Calc: C, 31.65; H, 3.79; N, 42.18; Cl, 13.35. Found: C, 31.36; H, 3.58; N, 41.26; Cl, 13.29.

EXAMPLE 2

Preparation of Methyl 3,5-diamino-6-cyano-2-pyrazinoate hemihydrate

Methyl 3,5-diamino-6-iodo-2-pyrazinoate (370 mg., 0.0012 mole), cuprous cyanide (215 mg., 0.0024 mole) and hexamethylphosphoramide (10 ml.) are combined and heated at 100° C. for 15 minutes. After cooling to 25° C. the reaction mixture is added to aqueous sodium cyanide solution, stirred at 25° C. for 1 hour and extracted with $CHCl_3$. The $CHCl_3$ layer was washed with dilute NaCN solution, then with $H_2O$, and dried $(MgSO_4)$. After evaporation of the $CHCl_3$, the residual oil was treated with hexane to give 75 mg. of methyl, 3,5-diamino-6-cyano-2-pyrazinoate hemihydrate melting at 284°–5° C.

Elemental analysis for $C_7H_7N_5O_2.\frac{1}{2}H_2O$; Calc: C, 41.59; H, 3.99; N, 34.64. Found: C, 42.81; H, 3.99; N, 34.09.

EXAMPLE 3

Preparation of N-Amidino-3,5-diamino-6-trifluoromethylthio-2-pyrazinecarboxamide Step A: Methyl 3,5-diamino-6-trifluoromethylthio-2-pyrazinoate Methyl 3,5-diamino-6-iodo-2-pyrazinoate (3.70 g., 0.0012 mole), cuprous trifluoromethylmercaptide (5.0 g., 0.0025 mole) and hexamethylphosphoramide (100 ml.) are combined and heated at 100° C. for 15 minutes. The reaction mixture is added to crushed ice—$H_2O$ and extracted with $CHCl_3$, the $CHCl_3$ layer washed with water, dried $(MgSO_4)$ then concentrated to give an amber oil. The oil is dissolved in ether, extracted several times with $H_2O$, dried $(MgSO_4)$ then concentrated to an oil which solidifies on trituration with butyl chloride to give 1.26 g. of methyl 3,5-diamino-6-trifluoromethylthio-2-pyrazinoate, m.p. 151°–5° C.

Elemental analysis for $C_7H_7F_3N_4O_2S$: Calc.: C, 31.35; H, 2.63; N, 20.89; S, 11.95. Found: C, 31.04; H, 2.67; N, 19.65; S, 11.95.

Step B: N-Amidino-3,5-diamino-6-trifluoromethylthio-2-pyrazinecarboxamide hydrate Guanidine hydrochloride (3.34 g., 0.035 mole) is added to a solution of sodium methoxide (1.67 g., 0.032 mole) in methanol (20 ml.) with stirring at 25° C. After 15 minutes, methyl 3,5-diamino-6-trifluoromethylthio-2-pyrazinoate (1.85 g., 0.007 mole) is added, and the mixture is heated on a steam bath for 15 min. Crushed ice—$H_2O$ (20 ml.) is added to the reaction mixture to precipitate 390 mg. of N-amidino-3,5-diamino-6-trifluoromethylthio-2-pyrazinecarboxamide, m.p. 195° C.

Elemental analysis for $C_7H_8F_3N_7OS.H_2O$; Calc: C, 26.84; H, 3.22; F, 18.19. Found: C, 27.09; H, 3.18; F, 17.49.

EXAMPLE 4

Step A: Methyl 3,5-diamino-6-trifluoromethylthio-2-pyrazinoate

Methyl 3,5-diamino-6-trifluoromethylthio-2-pyrazinoate is prepared from methyl 3,5-diamino-6-iodo-2-pyrazinoate following essentially the same procedure described in Example 3, Step A except that dimethylformamide is used as the solvent.

EXAMPLE 5

Step A: Methyl 3,5-diamino-6-trifluoromethylthio-2-pyrazinoate

Methyl 3,5-diamino-6-trifluoromethylthio-2-pyrazinoate is prepared from methyl 3,5-diamino-6-iodo-2-pyrazinate following essentially the same procedure described in Example 3, Step A except that bis(trifluoromethylthio)mercury and copper are used to generate cuprous trifluoromethylthiomercaptide in situ.

EXAMPLE 6

Step A: N-Amidino-3,5-diamino-6-trifluoromethylthio-2-pyrazinecarboxamide

N-Amidino-3,5-diamino-6-trifluoromethylthio-2-pyrazinecarboxamide is prepared from N-amidino-3,5-diamino-6-iodo-2-pyrazinecarboxamide hydrochloride by essentially the same procedure described in Example 1 using trifluoromethylthiocopper in place of cuprous cyanide.

EXAMPLE 7

Preparation of N-Amidino-3,5-diamino-6-methylthio-2-pyrazinecarboxamidehydrochloridehydrate Step A: Methyl 3,5-diamino-6-methylthiopyrazinoate A solution of methyl 3,5-diamino-6-iodopyrazinoate (14 g., 0.048 mole) and cuprous methylmercaptide (12 g., 0.108 mole) in hexamethylphosphoramide (100 ml.) is heated on a steam bath with stirring for $1\frac{1}{2}$ hours, poured into ice water (0.5 l) extracted with chloroform, washed with water, dried over $MgSO_4$ and evaporated at reduced pressure. Treatment of the residue with hexane gives 2.0 g. of methyl 3,5-diamino-6-methylthiopyrazinoate which melts at 158°–60° C. after purification by chromatography on silica gel; eluent 50% benzene-ethyl acetate.

Elemental analysis for $C_7H_{10}N_4O_2S$: Calc.: C, 39.25; H, 4.70; N, 26.16. Found: C, 40.16; H, 4.93; N, 26.58.

Step B: N-Amidino-3,5-diamino-6-methylthio-2-pyrazinecarboxamide hydrochloride hydrate Guanidine hydrochloride (1.5 g., 0.016 mole) is added to a solution of sodium methoxide (0.75 g., 0.014 mole) in methanol (25 ml.), stirred for five minutes and filtered free of sodium chloride. The guanidine solution is evaporated to 5 ml. then treated with methyl 3,5-diamino-6-methylthiopyrazinoate (0.6 g., 0.0028 mole) heated on a steam bath for five minutes, treated with water (10 ml.) and acidified with hydrochloric acid to give 0.6 g. of N-amidino-3,5-diamino-6-methylthio-2-pyrazinecarboxamide hydrochloride hydrate which melts at 170° C.

Elemental analysis for $C_7H_{11}N_7OS.HCl.H_2O$; Calc.: C, 28.42; H, 4.77; N, 33.15; Cl, 11.98. Found: C, 28.62; H, 4.44; N, 32.91; Cl, 12.11.

EXAMPLE 8

Preparation of N-Amidino-3,5-diamino-6-phenylthio-2-pyrazinecarboxamide hemihydrate Step A: Methyl 3,5-diamino-6-phenylthiopyrazinoate A mixture of methyl 3,5-diamino-6-iodopyrazinoate (3.5 g., 0.012 mole) and cuprous phenylmercaptide (2.3 g., 0.013 mole) in hexamethylphosphoramide (18 ml.) is heated on a steam bath for ten minutes and filtered. The filtrate is poured into 300 ml. of water, and the methyl 3,5-diamino-6-phenylthiopyrazinoate which separates melts at 210° C. after recyrstallization from 2-propanol.

Elemental analysis for $C_{12}H_{12}N_4O_2S$: Calc.: N, 20.28, H, 4.38. Found: N, 20.17; H, 4.40

Step B: N-Amidino-3,5-diamino-6-phenylthio-2-pyrazinecarboxamide hemihydrate

Guanidine hydrochloride (5.2 g., 0.055 mole) is added to a solution of sodium methoxide (2.7 g., 0.50 mole) in methanol (40 ml) stirred for five minutes and filtered free of sodium chloride. The guanidine solution is evaporated to a volume of 20 ml. then treated with methyl 3,5-diamino-6-phenylthiopyrazinoate (2.5 g., 0.009 mole), heated on a steam bath for ten minutes then poured into water (200 ml.) to give 2.2 g. N-amidino-3,5-diamino-6-phenylthio-2-pyrazinecarboxamide hemihydrate which melts at 238° C. after being washed with methanol.

Elemental analysis for $C_{12}H_{13}N_7OS \cdot \frac{1}{2}H_2O$: Calc.: C, 46.14; H, 4.52; N, 31.39. Found: C, 46.15; H, 4.59; N, 31.41.

EXAMPLE 9

Preparation of N-Amidino-3,5-diamino-6-chloro-2-pyrazinecarboxamide

N-Amidino-3,5-diamino-6-iodo-2-pyrazinecarboxamide (1.61 g., 0.005 mole), cuprous chloride (1.19 g., 0.012 mole) and hexamethylphosphoramide (15 ml.) are heated at 100° C. for 10 minutes. The mixture is cooled to 25° C. then added to aqueous sodium cyanide solution and extracted with $CHCl_3$. On evaporating the $CHCl_3$ and triturating the oily residue with hexane there is obtained N-amidino-3,5-diamino-6-chloro-2-pyrazinecarboxamide, m.p. 241° C.

Elemental analysis for $C_6H_8ClN_7O$; Calc.: C, 31.38; H, 3.51; N, 42.70; Cl, 15.44. Found: C, 31.59; H, 3.43; N, 42.85; Cl, 15.42.

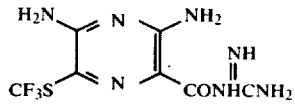

What is claimed is:

1. A compound of the formula: